(12) United States Patent
Collins et al.

(10) Patent No.: US 10,258,715 B1
(45) Date of Patent: Apr. 16, 2019

(54) ULTRAVIOLET DISINFECTION SYSTEM

(71) Applicant: RayVio Corporation, Hayward, CA (US)

(72) Inventors: Douglas A. Collins, Hayward, CA (US); Li Zhang, San Ramon, CA (US); Saijin Liu, Hayward, CA (US); Yitao Liao, Redwood City, CA (US)

(73) Assignee: RayVio Corporation, Hayward, CA (US)

( * ) Notice: Subject to any disclaimer, the term of this patent is extended or adjusted under 35 U.S.C. 154(b) by 0 days.

(21) Appl. No.: 15/905,593

(22) Filed: Feb. 26, 2018

(51) Int. Cl.
| | |
|---|---|
| A61L 9/00 | (2006.01) |
| A61L 9/20 | (2006.01) |
| H01L 33/48 | (2010.01) |
| H01L 33/32 | (2010.01) |
| H01L 33/06 | (2010.01) |
| H01L 27/15 | (2006.01) |
| H01L 33/40 | (2010.01) |
| H01L 33/58 | (2010.01) |
| C02F 1/32 | (2006.01) |
| H01L 25/16 | (2006.01) |
| H01L 33/20 | (2010.01) |

(52) U.S. Cl.
CPC ............... *A61L 9/20* (2013.01); *C02F 1/32* (2013.01); *H01L 25/167* (2013.01); *H01L 27/156* (2013.01); *H01L 33/06* (2013.01); *H01L 33/32* (2013.01); *H01L 33/405* (2013.01); *H01L 33/483* (2013.01); *H01L 33/58* (2013.01); *A61L 2209/111* (2013.01); *A61L 2209/12* (2013.01); *C02F 2201/326* (2013.01); *C02F 2201/3228* (2013.01); *C02F 2303/04* (2013.01); *C02F 2307/02* (2013.01); *H01L 33/20* (2013.01); *H01L 33/325* (2013.01)

(58) Field of Classification Search
CPC .. A61L 9/20; A61L 2209/111; A61L 2209/12; C02F 1/32; C02F 2201/3228; C02F 2201/326; C02F 2303/04; C02F 2303/02; H01L 25/167; H01L 27/156; H01L 33/06; H01L 33/32; H01L 33/405; H01L 33/483; H01L 33/58; H01L 33/20; H01L 33/3258
USPC .................. 250/453.11, 454.11, 455.11
See application file for complete search history.

(56) References Cited

U.S. PATENT DOCUMENTS 7,857,485 B2 * 12/2010 Wang ............... H01L 33/60
257/98

* cited by examiner

*Primary Examiner* — Nicole Ippolito
*Assistant Examiner* — Hanway Chang
(74) *Attorney, Agent, or Firm* — Patent Law Group LLP; Brian D. Ogonowsky

(57) ABSTRACT

Embodiments of the invention include a vessel having an opening and a detachable cover for covering the opening. The cover includes a semiconductor device with an active layer disposed between an n-type region and a p-type region. The active layer emits radiation having a peak wavelength in a UV range. The cover also includes a sensor for detecting whether the cover is covering the opening.

18 Claims, 3 Drawing Sheets

ULTRAVIOLET DISINFECTION SYSTEM

BACKGROUND

Description of Related Art

The bandgap of III-nitride materials, including (Al, Ga, In)—N and their alloys, extends from the very narrow gap of InN (0.7 eV) to the very wide gap of AlN (6.2 eV), making III-nitride materials highly suitable for optoelectronic applications such as light emitting diodes (LEDs), laser diodes, optical modulators, and detectors over a wide spectral range extending from the near infrared to the deep ultraviolet. Visible light LEDs and lasers can be obtained using InGaN in the active layers, while ultraviolet (UV) LEDs and lasers require the larger bandgap of AlGaN.

UV LEDs with emission wavelengths in the range of 230-350 nm are expected to find a wide range of applications, most of which are based on the interaction between UV radiation and biological material. Typical applications include surface sterilization, water purification, medical devices and biochemistry, light sources for ultra-high density optical recording, white lighting, fluorescence analysis, sensing, and zero-emission automobiles. UV radiation has disinfection properties that inactivate bacteria, viruses, and other microorganisms. Since most microorganisms are affected by radiation around 260 nm, UV radiation is in the appropriate range for germicidal activity.

DETAILED DESCRIPTION

Though the devices described herein are III-nitride devices, devices formed from other materials such as other III-V materials, II-VI materials, Si are within the scope of embodiments of the invention. The devices described herein may be configured to emit UV A (peak wavelength between 340 and 400 nm), UV B (peak wavelength between 290 and 340 nm), or UV C (peak wavelength between 210 and 290 nm) radiation. UV radiation or radiative power may be referred to herein as "light" for economy of language.

In embodiments of the invention, one or more UVLEDs are used in a disinfection device, suitable for disinfecting a fluid, such as water, air, or any other suitable material. Though disinfection devices are described, the structures, devices, and methods described herein may be used in any suitable application.

In some embodiments, the disinfection devices described herein are used to disinfect drinking water, other liquids or solids intended for human or animal consumption. In some embodiments, all materials used in the disinfection devices are food-safe. In some embodiments, all materials that contact the vessel, material, water, or fluid to be disinfected in the disinfection devices are food-safe.

Figure 3:
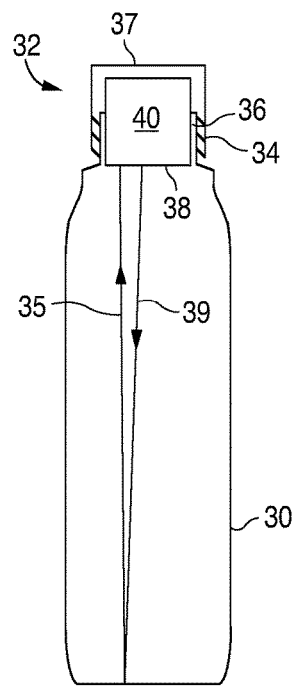
FIG. 3 illustrates a disinfection device including a vessel, a cover, and a UV light source.

FIG. 3 illustrates a disinfection device according to some embodiments. The device of FIG. 3 may be, for example, a water bottle.

The device of FIG. 3 includes a vessel 30, inside of which a fluid or other material to be disinfected may be placed. The vessel 30 may be rigid in some embodiments, though this is not required. The vessel 30 may be opaque in some embodiments, though this is not required. The vessel 30 may be elongate in some embodiments; the length may be, for example, at least two times greater than the width in some embodiments, and no more than a hundred times greater than the width in some embodiments. The cross section of vessel 30 may be circular, oval, square, rectangular, hexagonal, or any other suitable shape. The vessel 30 may be made from plastic, metal, glass, or any suitable material.

In some embodiments, the interior walls of the vessel, i.e. the walls that contact the fluid or material, are UV reflective. The reflectance of the interior walls may be greater than 30% for UV light with wavelengths in the range of 250-290 nm.

In some embodiments, the vessel itself may be made from a UV reflective material, such as for example, polished stainless steel or any other suitable material.

In some embodiments, the interior walls of the vessel may be a UV reflective material that is coated on a different material such as glass or plastic, or formed into a film and attached to a different material. Examples of suitable reflective coatings include metals, silver, aluminum, Teflon, polytetrafluoroethylene (PTFE), barium sulfate, oxides, oxides of silicon including $SiO_2$, oxides of aluminum including $Al_2O_3$, oxides of yttrium, oxides of hafnium, a multilayer stack, a distributed Bragg reflector, and combinations thereof. A reflective coating may be covered by a protective layer, such as, for example, one or more oxides of silicon including $SiO_2$, oxides of aluminum including $Al_2O_3$, or any other suitable material.

In some embodiments, the interior walls reflect UV light by total internal reflection (TIR) or attenuated total internal reflection (ATR), where the material is reflective but somewhat absorbing, such that some power is lost when radiation is incident on the ATR material. A TIR material may be preferred in some embodiments for better reflection, but an ATR material may be used for other reasons such as cost, durability, etc. Water has an index of refraction of about 1.35 for UV light near 280 nm. In one embodiment, the interior walls of the vessel may be a liner such as a molded polymer that has a smooth inner surface and an index of below about 1.33 (somewhat below that of water) to enable TIR to occur. Examples of suitable liners include Teflon, Fluorilon 99-U, MY-133-V2000, available from MY Polymers Ltd, and Topas' 8007 polymer available from Topas Advanced Polymers, GmbH. Other polymers or other materials with other suitable indices are also available. With TIR, there is essentially no reflective loss (reflectivity >99.5%), as compared to a reflective material such as a polished metal (reflectivity about 90-95%). The liner is not considered a reflector and may be transparent. The liner may be formed on a UV reflective material, such as aluminum, chrome, or silver, to reflect any light that is above the critical angle and passes through the transparent liner. To mitigate the effects of waveguiding within the liner, the surface on which the liner is disposed (the surface that is protected from the fluid by the liner) may include molded prisms or roughening to cause scattering.

In some embodiments, the interior walls of vessel 30 have a generally parabolic or other suitable shape to direct impinging UV radiative power into the fluid in the vessel or toward another area of the interior walls. The UV light source may be positioned such that radiative power emitted substantially horizontally impinges on a curved portion of the interior wall and is redirected.

Suitable reflective surfaces and shaped surfaces are described in more detail in U.S. application Ser. No. 15/820,184, which is incorporated herein by reference.

In some embodiments, one or more surfaces of the vessel 30 that encounter water may be coated with or otherwise treated with a photocatalytic material such as $TiO_2$. $TiO_2$ may photocatalyze water into OH radicals, which may purify water by breaking down organic material.

In some embodiments, insulation to keep a fluid hot or cold for example, may be disposed between the interior walls of the vessel and the exterior walls of the vessel. In some embodiments, the insulation is a vacuum space between the interior walls of the vessel and the exterior walls of the vessel.

A UV light source such as a UV LED may be housed in a cover 32. The UV light source introduces UV radiative power 39 into the vessel 30, and any fluid contained in the vessel 30. The reflected UV radiative power 35 may disinfect the interior surface of cover 32 and the entrance portion of vessel 30. The cover 32 may seal the vessel 30, though this is not required. In the example illustrated in FIG. 3, threads 34 on the cover 32 engage with threads 36 on the vessel 30 to form a watertight or fluid-tight seal. Any other suitable closure besides threads, such as a clamp, press-fit, or other closure may be used.

The cover 32 may include a chamber 40, within which components such as the UV light source, detectors, circuit boards, controllers, and other structures described below may be housed. The chamber 40 is often watertight or fluid-tight, though this is not required in all embodiments. A top surface 37 of the cover 32, outside the closed vessel, may receive user inputs and/or display information to a user, for example in the form of colored indicator lights. A bottom surface 38 of the cover, within the closed vessel and directed toward fluid contained in the vessel, may include the UV light source and one or more sensors. Examples of the top and bottom surfaces are described below and illustrated in FIGS. 5 and 6.

Figure 1:
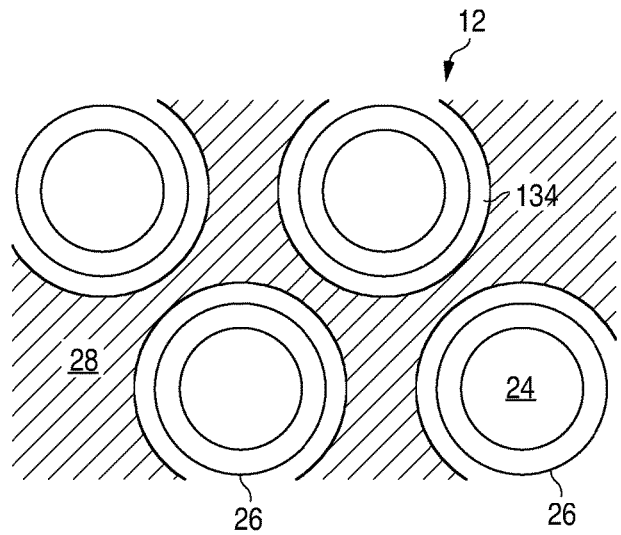
FIG. 1 is a plan view of multiple pixels in a flip chip UV-emitting device (UVLED).
Figure 2:
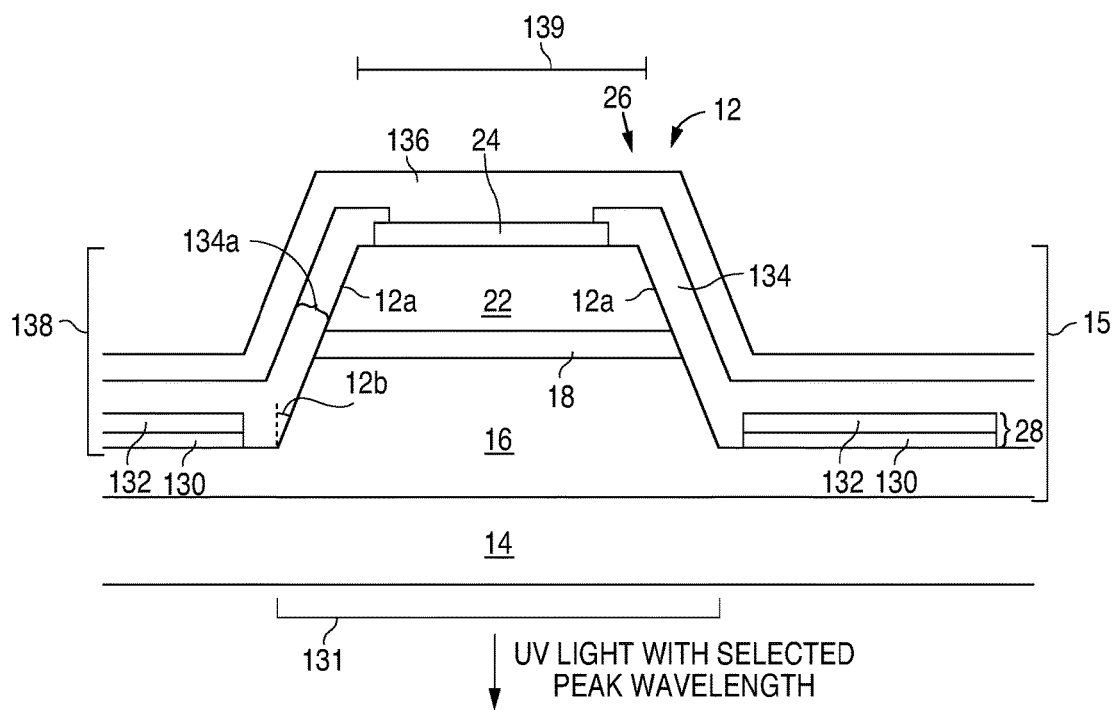
FIG. 2 is a cross sectional view of one pixel in the UVLED of FIG. 1.

Commercially available UVA, UVB, and UVC LEDs may be used as a UV light source in various embodiments. FIGS. 1 and 2 are examples of the assignee's own UVB and UVC LEDs that may be used. FIG. 1 is a top down view of a portion of an array of UVLED pixels 12, and FIG. 2 is a bisected cross-section of a single UVLED pixel 12. Any suitable UVLED may be used and embodiments of the invention are not limited to the device of FIGS. 1 and 2.

The UVLEDs are typically III-nitride, and commonly GaN, AlGaN, and InGaN. The array of UV emitting pixels 12 is formed on a single substrate 14, such as a transparent sapphire substrate. Other substrates are possible. Although the example shows the pixels 12 being round, they may have any shape, such as square. The light escapes through the transparent substrate, as shown in FIG. 2. The pixels 12 may each be flip-chips, where the anode and cathode electrodes face the mount (described below).

All semiconductor layers are epitaxially grown over the substrate 14. An AlN or other suitable buffer layer (not shown) is grown, followed by an n-type region 16. The n-type region 16 may include multiple layers of different compositions, dopant concentrations, and thicknesses. The n-type region 16 may include at least one $Al_aGa_{1-a}N$ film doped n-type with Si, Ge and/or other suitable n-type dopants. The n-type region 16 may have a thickness from about 100 nm to about 10 microns and is grown directly on the buffer layer(s). The doping level of Si in the n-type region 16 may range from $1\times10^{16}$ cm$^{-3}$ to $1\times10^{21}$ cm$^{-3}$. Depending on the intended emission wavelength, the AlN mole fraction "a" in the formula may vary from 0% for devices emitting at 360 nm to 100% for devices designed to emit at 200 nm.

An active region 18 is grown over the n-type region 16. The active region 18 may include either a single quantum well or multiple quantum wells (MQWs) separated by barrier layers. The quantum well and barrier layers contain $Al_xGa_{1-x}N/Al_yGa_{1-y}N$, wherein $0<x<y<1$, x represents the AlN mole fraction of a quantum well layer, and y represents the AlN mole fraction of a barrier layer. The peak wavelength emitted by a UV LED is generally dependent upon the relative content of Al in the AlGaN quantum well active layer. The active region may emit radiative power with a peak wavelength between 260 nm and 290 nm in some embodiments, between 250 nm and 350 nm in some embodiments, and 280 nm in some embodiments.

A p-type region 22 is grown over the active region 18. Like the n-type region 16, the p-type region 22 may include multiple layers of different compositions, dopant concentrations, and thicknesses. The p-type region 22 includes one or more p-type doped (e.g. Mg-doped) AlGaN layers. The AlN mole fraction can range from 0 to 100%, and the thickness of this layer or multilayer can range from about 2 nm to about 100 nm (single layer) or to about 500 nm (multilayer). A multilayer used in this region can improve lateral conductivity. The Mg doping level may vary from $1\times10^{16}$ cm$^{-3}$ to $1\times10^{21}$ cm$^{-3}$. A Mg-doped GaN contact layer may be grown last in the p-type region 22.

All or some of the semiconductor layers described above may be grown under excess Ga conditions, as described in more detail in US 2014/0103289, which is incorporated herein by reference.

The semiconductor structure 15 is etched to form trenches between the pixels 12 that reveal a surface of the n-type region 16. The sidewalls 12a of the pixels 12 may be vertical or sloped with an acute angle 12b relative to a normal to a major surface of the growth substrate. The height 138 of each pixel 12 may be between 0.1-5 microns. The widths 131 and 139 at the bottom and top of each pixel 12 may be at least 5 microns. Other dimensions may also be used.

Before or after etching the semiconductor structure 15 to form the trenches, a metal p-contact 24 is deposited and patterned on the top of each pixel 12. The p-contact 24 may include one or more metal layers that form an ohmic contact, and one or more metal layers that form a reflector. One example of a suitable p-contact 24 includes a Ni/Ag/Ti multi-layer contact.

An n-contact 28 is deposited and patterned, such that n-contact 28 is disposed on the substantially flat surface of the n-type region 16 between the pixels 12. The n-contact 28 may include a single or multiple metal layers. The n-contact 28 may include, for example, an ohmic n-contact 130 in direct contact with the n-type region 16, and an n-trace metal layer 132 formed over the ohmic n-contact 130. The ohmic n-contact 130 may be, for example, a V/Al/Ti multi-layer contact. The n-trace metal 132 may be, for example, a Ti/Au/Ti multi-layer contact.

The n-contact 28 and the p-contact 24 are electrically isolated by a dielectric layer 134. Dielectric layer 134 may be any suitable material such as, for example, one or more oxides of silicon, and/or one or more nitrides of silicon, formed by any suitable method. Dielectric layer 134 covers n-contact 28. Openings formed in dielectric layer 134 expose p-contact 24.

A p-trace metal 136 is formed over the top surface of the device, and substantially conformally covers the entire top surface. The p-trace metal 136 electrically connects to the p-contact 24 in the openings formed in dielectric layer 134. The p-trace metal 136 is electrically isolated from n-contact 28 by dielectric layer 134.

FIG. 1 is a top view of four of the pixels illustrated in FIG. 2. The p-trace metal 136, which covers the entire surface, is omitted for clarity. The p-contact 24 is smaller than and substantially concentric with the edge 26 of the mesa that forms each pixel 12. The n-contact 28 is disposed in the region between the pixels 12. Except for openings in the n-contact 28 to accommodate the pixels, the n-contact 28 forms a continuous sheet, which extends to the edge of the device into n-contact pad (not shown). The n-contact 28 and p-contact 24 are electrically isolated by dielectric layer 134, which extends over the sidewalls of each pixel, as illustrated in FIG. 2.

Robust metal pads electrically connected to the p-trace metal 136 and n-contact 28 are provided outside of the drawing for connection to power supply terminals. Multiple pixels 12 are included in a single UVLED. The pixels are electrically connected by large area p-trace metal 136 and the large area n-trace metal 132. The number of pixels may be selected based on the application and/or desired radiation output. A single UVLED, which includes multiple pixels, is illustrated in the following figures as UVLED 1.

In some embodiments, substrate 14 is sapphire. Substrate 14 may be, for example, on the order of hundreds of microns thick. In a 1 mm square UVLED 1 with a 200 µm thick sapphire substrate, assuming radiation is extracted from the top and sides of the substrate, the top surface accounts for about 55% of the extraction surface, and the sides account for about 45% of the extraction surface of the substrate. Substrate 14 may remain part of the device in some embodiments, and may be removed from the semiconductor structure in some embodiments.

The UVLED may be square, rectangular, or any other suitable shape when viewed from the top surface of substrate 14, when the device is flipped relative to the orientation illustrated in FIG. 2.

Figure 4:
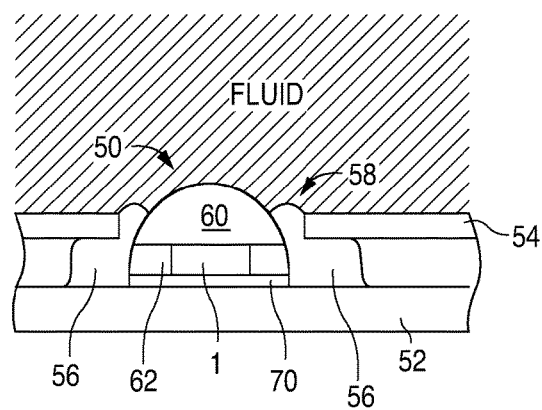
FIG. 4 illustrates a package including a UVLED, a mount, and a cover.

The UVLED illustrated in FIGS. 1 and 2 may be disposed in a package. The package primarily directs light from the UVLED in a useful manner, protects the UVLED, provides electrical connection to the UVLED, and removes heat from the UVLED. FIG. 4 illustrates one example of a suitable package. Any suitable package or other suitable structure which performs some or all of the functions described above may be used. The package generally includes a mount 70 and a cover 60.

The UVLED 1 is physically attached to mount 70. The mount may be configured to provide electrical connections to the UVLED 1, and to remove heat from the UVLED 1. Mount 70 may be attached to a structure such as a circuit board 52. The circuit board 52 is not part of the package 50 and is included in FIG. 4 for clarity. The mount 70 may be, for example, a ceramic mount, aluminum nitride, a circuit board, a metal-core printed circuit board, a silicon mount, or any other suitable structure. Circuit elements such as driver circuitry for UVLED 1 or any other suitable circuitry may be disposed on or within mount 70. More than one UVLED may be attached to mount 70. In each of the disinfection devices described below, a single UVLED may be used, multiple UVLEDs disposed in a single package may be used, or multiple packages including one or more UVLEDs each may be used, in order to provide UV radiation sufficient for disinfection in the disinfection device.

In some embodiments, a reflector cup (not shown) is formed in the mount 70 or disposed on the mount 70, surrounding UVLED 1.

The cover 60 is usually a lens as illustrated in FIG. 4, but can be any structure that couples UV radiative power into the vessel and/or a fluid or other material in the vessel. For economy of language, the cover 60 may be referred to herein as an optic, though embodiments are not limited to an optic or a lens. The cover 60 may be attached to UVLED 1 and/or to mount 70 by an adhesive 62, though this is not required.

The optic 60 may be any suitable optic, including for example, the dome lens illustrated, a Fresnel lens, a compound parabolic collimator, a total internal reflective lens, or any other suitable lens or optic. The optic 60 may create a radiation pattern that is more collimated than the radiation pattern emitted by the UVLED 1 without the optic 60. In some embodiments, the optic 60 is a compound parabolic collimator. UV radiation encountering a curved sidewall is reflected toward an outlet surface.

Cover 60 may be a truncated inverted pyramid or cone. The outlet surface of the cover 60 may be, for example, rotationally symmetric, oval, round, square, rectangular, or any other suitable shape. The shape of the outlet surface of cover 60 may be matched to the shape of the disinfection vessel. The surface of the cover 60 that is optically coupled to the top surface of the UVLED may be only slightly larger than the top surface of the UVLED; no more than 10% larger in some embodiments, no more than 20% larger in some embodiments, and no more than 30% larger in some embodiments. In some embodiments, a lens or other optic is disposed over UVLED 1, between the UVLED 1 and cover 60, or cover 60 is disposed between UVLED 1 and another lens or other optic.

A solid optic 60 is formed from a material that is transparent to UV radiation at wavelengths emitted by UVLED 1, and able to withstand the UV radiation without degrading. For example, in some embodiments, the optic may be formed from a material that transmits at least 85% of UV radiation at 280 nm. The material may degrade no more than 1% after 1000 hrs of exposure to UV radiation at 280 nm. In some embodiments, optic 60 is formed from a material that is moldable, such as, for example, glass, IHU UV transmissive glass available from Isuzu Glass, Inc., and UV-resistant silicone. In some embodiments, optic 60 is formed from a material that may be shaped by, for example, grinding and polishing, such as quartz, fused silica, or sapphire. An optic formed by molding may be less expensive; an optic formed by grinding and polishing may be of better optical quality.

In some embodiments, cover 60 is optically coupled to only the top surface of the UVLED 1, typically a surface of the growth substrate, or a major surface of the semiconductor structure of UVLED 1. In some embodiments, cover 60 may extend over and be optically coupled to the sides of UVLED 1 as well. Cover 60 may extend over the sides of just the growth substrate, or over the sides of both the growth substrate and the semiconductor structure.

In some embodiments, only the top surface of UVLED 1 is optically coupled to the optic 60. The side surfaces of UVLED 1 are not optically coupled to the optic, such that radiation emitted from the side surfaces is lost. Capturing the radiation from just the top surface increases the etendue of the UVLED/optic system. Increasing the etendue may increase the irradiance of the system and reduce the source size, which may be useful for some applications. The radiation emitted to the side is discarded in these embodiments, though in UV-emitting systems, radiation may preferentially be emitted toward the side surfaces of a UVLED, rather than the top surface of the UVLED, due to polarization within the AlGaN active layer(s).

In the structure illustrated in FIG. 4, the packaged UV device 50, which includes the UVLED 1, mount 70, cover 60, and adhesive 62 (if used), is attached to a structure 52 such as a printed circuit board (PCB). The PCB 52 is disposed within the chamber 40 in cover 32 (illustrated in FIG. 3). A wall 54 of the chamber 40, the wall 54 facing the vessel and/or any fluid or material in the vessel (surface 38 in FIG. 3) is fluid-tight. An opening 58 is formed in wall 54, so that the optic 60 of UV source 50 may protrude from the chamber 40 (FIG. 3). A fluid-tight seal 58 is disposed between the UV source 50 and the wall 54. The fluid-tight seal 58 may be silicone, epoxy, or any other suitable material. The wall 54 may be, for example, silicone, plastic, stainless steel, or any other suitable material. The fluid-tight seal 58 and wall 54 may be food safe materials, as described above. In some embodiments, no opening is formed and the wall 54 is disposed between the fluid to be disinfected and the UV source 50. In such embodiments, the wall 54 must transmit UV radiative power from the UV source 50 into the fluid.

Figure 5:
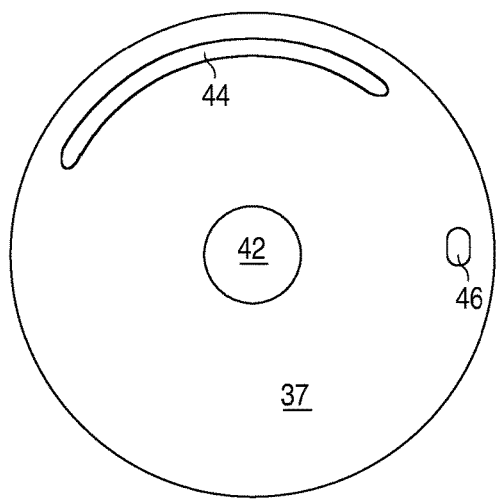
FIG. 5 illustrates the top surface of the cover of FIG. 3, in some embodiments.
Figure 6:
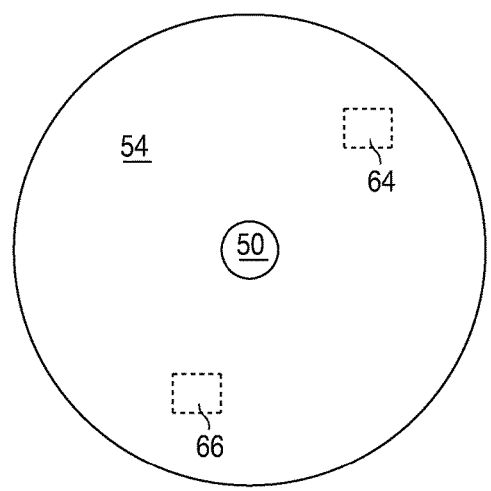
FIG. 6 illustrates the bottom surface of the cover of FIG. 3, in some embodiments.
Figure 7:
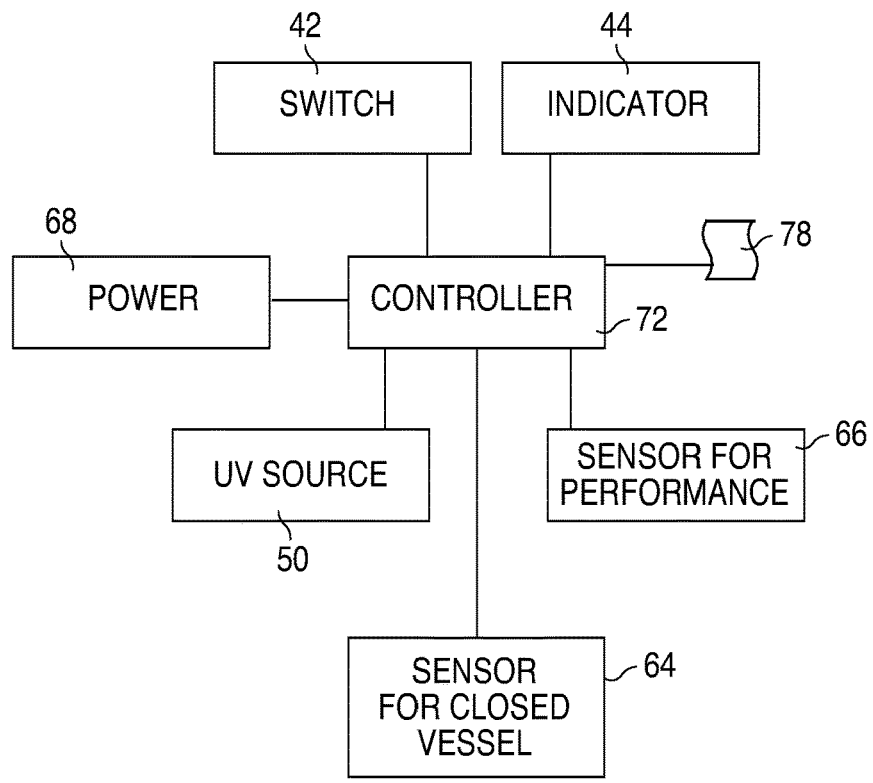
FIG. 7 is a block diagram of a system for operating the device of FIG. 3.

FIG. 5 illustrates the top surface of the cover of FIG. 3, according to some embodiments. FIG. 6 illustrates the bottom surface of the cover of FIG. 3, according to some embodiments. FIG. 7 illustrates a system for operating the device of FIG. 3, according to some embodiments, including the components illustrated in FIGS. 5 and 6. Not all of the components illustrated in FIG. 7 are included in all embodiments. The system illustrated in FIG. 7 may be housed in the chamber 40 of cover 32, illustrated in FIG. 3. In some embodiments, only some of the components are included. Other components that are not shown may be used in some embodiments.

In the system illustrated in FIG. 7, a controller 72 coupled to UV source 50 controls UV source 50, which may include a UVLED in a package according to embodiments described above. Controller 72 may be a microprocessor or any other suitable structure. A power source 68, such as a battery, is coupled to controller 72. Power source 68 supplies power to activate UV source 50 via controller 72. Power source 68 also supplies power to other components, such as indictor(s) 44, via controller 72. In some embodiments, user access 46 to the power source 68 is provided in a part of the cover that is accessible to the user (access 46 is shown in FIG. 5 on the top of the cover, though this is not required—access 46 may be disposed on the side of the cover or any other suitable location). User access 46 may be, for example, a door that allows the user to change batteries, or a port such as a USB or other suitable port for charging a rechargeable battery.

A switch 42 may be coupled to the controller 72, to receive user inputs. For example, user may press a switch 42, disposed on the top of the cover in FIG. 5, in order to start disinfecting a fluid in the vessel. Switch may be a touch sensor in some embodiments, or any other suitable switch.

One or more indicators 44 may be coupled to controller 72. Indicators 44 may be visual indicators such as lights, audio indicators, sensory indicators such as a device to cause vibration, or any other suitable indicator. Indicators communicate the status of the device to a user. Accordingly, visual indicators 44 such as colored LEDs are visible in region 44 on the top surface of the cover illustrated in FIG. 5. Different indicator states, including, for example, different colors, different patterns of flashing, or any other suitable manner may be used to communicate different statuses. For example, a flashing blue light may be a first indicator state that indicates the device is disinfecting water, a solid green light may be a second indicator state that indicates the disinfection operation is complete, a solid red light may be a third indicator state that indicates the device is not functioning properly, a flashing red light may be a fourth indicator state that indicates a low battery, etc.

One or more sensors 64 for detecting whether the vessel is closed may be coupled to controller 72. Sensor 64 may protect a user from injury from activation of UV source 50 when the vessel is not closed. Sensor 64 may be, in some embodiments, a visible light sensor disposed on the bottom of the cover, as illustrated in FIG. 6. Visible light sensor may detect light with a wavelength between 400 nm and 700 nm. Vessel 30 and cover 32 may be opaque in this embodiment. In operation, a user activates switch 42 to indicate that disinfection (activating UV source 50) should begin. Controller 72 checks visible light sensor 64—if visible light is detected, the vessel is not closed. Controller 72 may then activate an indicator state that signifies an error. If no visible light is detected, controller 72 may activate UV source 50. Controller 72 may then activate an indicator state that the UV source 50 is on.

Figure 8:
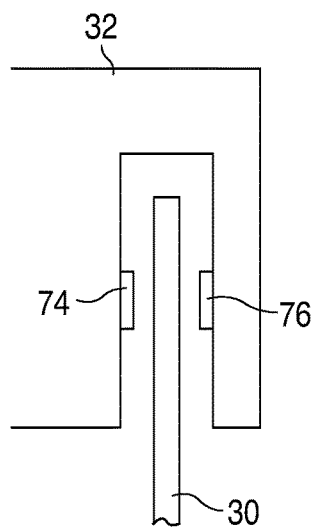
FIG. 8 illustrates an infrared source and sensor for detecting whether the vessel of FIG. 3 is closed.

A passive visible light sensor, such as the sensor described above, may inaccurately indicate the cover is covering the vessel in certain situations. For example, if the vessel is in a dark area, or the device is used at night, the visible light sensor may not detect visible light even when the vessel is not closed. In some embodiments, sensor 64 may be an active sensor mechanism. It comprises a light source paired with a sensor or detector, as illustrated in FIG. 8. In some embodiments the light source is, for example, an infrared source, or a visible light source. The detector may be matched with the light source. The light source may have a peak wavelength between 400 nm and 1000 nm; the detector may detect light between 400 nm and 1000 nm. FIG. 8 illustrates a cross section of a portion of the cover 32 and vessel 30. The cover includes a recess where, when closed, the vessel interposes opposite sides of the recess. The recess may be, for example, the threaded area in a screw-on cover. A light source 74 is disposed on one side of the recess; a detector 76 is disposed on the other side of the recess opposite the source 74. The portion of the vessel that interposes the parts of the cover is opaque to radiation emitted by the light source. When the cover is on the vessel, closing the vessel, the detector will not detect radiation from the light source 74, because the opaque vessel will prevent radiation from the source from reaching the detector. When the cover is not on the vessel, meaning the vessel is open, the detector will detect radiation from the light source 74. In operation, a user activates switch 42 to indicate that disinfection (activating UV source 50) should begin. Controller 72 activates light source 74 and checks detector 76. If radiation from the light source 74 is detected, the vessel is not closed; controller 72 may then activate an indicator state that signifies an error. If no radiation from light source 74 is detected, controller 72 may activate UV source 50. Controller 72 may then activate an indicator state that signifies disinfection is occurring.

One or more sensors 66 for detecting whether the UV source 50 and/or other components are performing as intended may be coupled to controller 72. In some embodiments, a thermistor is included as a sensor 66. A thermistor is positioned close to UV source 50, and detects the temperature in the vicinity of UV source 50. The thermistor may detect three temperature regimes. Below a temperature $T_1$, the operating UV source 50 is operating in optimal temperature conditions. Many UV sources are sensitive to operating temperature and experience diminished UV output at elevated temperature. Accordingly, above a temperature $T_2$, the operating UV source 50 may experience diminished UV output. When the thermistor indicates a temperature above $T_2$, the controller may, alone or in combination, (1) activate indicator(s) 44 to a state that signifies the device is not operating properly or the fluid is not disinfected, (2) increase the current supplied to UV source 50 for a limited duration, in order to provide enough UV radiation to disinfect during a predefined time period, or (3) increase the amount of time that the UV source 50 is activated, in order to provide enough UV radiation to disinfect. Above a temperature $T_3$, the UV source 50 may be damaged. When the thermistor indicates a temperature above $T_3$, the controller may stop supplying power to UV source 50, and/or activate indicator(s) 44 to a state that signifies that the device is not operating properly or the fluid is not disinfected. $T_2$ may be, for example, 60-65° C. in some embodiments; $T_3$ may be, for example, 115-120° C. in some embodiments.

In some embodiments, a UV detector is included as a sensor 66. The UV detector measures the amount of UV radiative power in the vessel. The amount of UV radiative power emitted by source 50 may be adjusted accordingly by controller 72, for example by increasing or decreasing the current to UV source 50, or by increasing or decreasing the time UV source 50 is activated. A second UV detector may be used to detect whether the UV source 50 is functioning properly. For example, the first UV detector may be positioned near UV source 50, and second detector may be positioned far from UV source 50. When UV source 50 is on, the amount of UV radiation detected by each of the detectors may be compared. If the first detector indicates a higher amount of UV radiation and the second detector indicates a lower amount of UV radiation, the fluid may be contaminated with particulate matter. If both detectors indicate a low amount of UV radiation, the UV radiation 50 may not be functioning properly. Controller may cause indicator 44 to indicate to a user that UV source 50 is not functioning properly.

A computer readable memory 78 encoded with instructions to carry out the operations described herein may be coupled to controller 72.

FIG. 6 illustrates a portion of the bottom of cover 32 of FIG. 3, according to some embodiments. A wall 54 seals the chamber 40 illustrated in FIG. 3 such that it is fluid-tight, to protect the components illustrated in FIG. 7 from the fluid in vessel 30. Sensors 64 and 66 are illustrated by dashed lines to indicate that they are separated from the fluid by wall 54. UV source 50 is disposed in a fluid-tight opening in wall 54, as illustrated in FIG. 4.

The components illustrated in FIG. 7 may be disposed on or in the mount, described above, and/or on or in one or more separate circuit boards, described above. The components may be electrically connected to each other as illustrated via the mount, one or more circuit boards, or any other suitable structure.

In one operation, a user activates switch 42. If sensor 64 detects the vessel is closed, controller 72 supplies power from the power source to UV source 50. Controller 72 may also change indicator 44 to a state indicating the UV source is disinfecting. The amount of time that the fluid or vessel is exposed to radiation from UV source may be dictated by a timer, which may count a predetermined amount of time, after which controller 72 may turn off UV source 50. Controller 72 may then switch indicator 44 to a state indicating disinfection is complete. Alternatively, the amount of UV radiation may be measured by detector 66. In response, controller 72 may adjust the amount of time that the UV source 50 stays on, and/or the power to UV radiation source 50, in order to deliver a sufficient dose of UV radiation to disinfect the fluid or vessel. Once the dose is reached, controller 72 may turn off UV source 50, and change indicator 44 to a state indicating the UV source is finished disinfecting.

In some embodiments, the device may include a filter, which may be any suitable structure through which fluid may pass. Filters may filter out some or all particulate matter in the fluid, though this is not required. Filters may also be reflective of UV radiation. Filters may be any suitable material including, for example, porous aluminum, aluminum screens, or Teflon particles sintered into porous Teflon made by Porex, Inc. For example, a filter may be disposed near the opening in vessel 30.

In some embodiments, the device may include one or more sonication devices. The sonication devices apply sound energy to agitate the fluid. Any suitable frequency may be used. Suitable frequencies are often greater than 20 kHz in some embodiments, and no more than 400 kHz in some embodiments. Thorough disinfection requires that the UV radiation dose be distributed uniformly, so all of the fluid "see" the UV radiation for a time long enough for disinfection. Sonication mixes the fluid which helps distribute the UV radiation dose. In addition, the presence of particulate matter in fluid samples hinders UV disinfection because the UV radiation is scattered, and bacteria may be shaded by particles or incorporated into flocs. Sonication may reduce the shading effect from particulate matter and may help deagglomerate microbe clusters such as *E. Coli, Legionella, Shigella*, etc. by mechanical force. Sonication may be particularly useful in embodiments where limited UVLEDs can be used, for example due to cost limitations, space limitations, fluid volume, etc.

In some embodiments, one or more piezoelectric sonicator discs are disposed inside the vessel 30 or cover 32. The piezoelectric sonicator discs may be in contact with the fluid, directly or through a sealing material disposed over the piezoelectric sonicator discs. In some embodiments, a sonicator is disposed in the fluid to be disinfected. The sonicator may be attached, for example, to an external mechanical support. The external mechanical support may be attached, for example, to the vessel or cover.

Having described the invention in detail, those skilled in the art will appreciate that, given the present disclosure, modifications may be made to the invention without departing from the spirit of the inventive concept described herein. In particular, different features and components of the different devices described herein may be used in any of the other devices, or features and components may be omitted from any of the devices. A characteristic of, for example, the sidewall of the vessel or the cover in the UVLED package, described in the context of one embodiment, may be applicable to any embodiment. Suitable materials described for a particular component in a particular embodiment may be used for other components, and/or in other embodiments. Therefore, it is not intended that the scope of the invention be limited to the specific embodiments illustrated and described.

What is being claimed is:

1. A device comprising:
a vessel comprising an opening; and
a detachable cover for covering the opening, the cover comprising:
- a semiconductor device comprising an active layer disposed between an n-type region and a p-type region, wherein the active layer emits radiation having a peak wavelength in a UV range; and
- a sensor for detecting whether the cover is covering the opening.

2. The device of claim 1 wherein the sensor is a detector of light.

3. The device of claim 1 wherein an inner surface of the vessel comprises a food safe material.

4. The device of claim 1 wherein the cover further comprises a thermistor.

5. The device of claim 1 wherein the cover further comprises a controller for supplying current to the semiconductor device.

6. The device of claim 5 wherein the cover further comprises a computer readable memory encoded with instructions for:
the controller receiving a user-generated input from a switch; and
the controller supplying current to the semiconductor device if the sensor indicates the cover is covering the opening.

7. The device of claim 6 wherein:
the cover further comprises an indicator; and
the computer readable memory further comprises instructions for:
activating a first indicator state if the sensor indicates the cover is not covering the opening; and
activating a second indicator state if the controller is supplying current to the semiconductor device.

8. The device of claim 7 wherein:
the indicator comprises a first light of a first color and a second light of a second color;
activating a first indicator state comprises activating the first light; and
activating a second indicator state comprises activating the second light.

9. The device of claim 6 wherein:
the cover further comprises a UV detector; and
the computer readable memory further comprises instructions for adjusting an amount of current supplied to the semiconductor device or a time current is supplied to the semiconductor device based on an output of the UV detector.

10. The device of claim 1 wherein an inner surface of the vessel comprises a UV reflective material.

11. A device comprising:
a vessel comprising an opening; and
a detachable cover for covering the opening, the cover comprising:
- a semiconductor device comprising an active layer disposed between an n-type region and a p-type region, wherein the active layer emits radiation having a peak wavelength in a UV range; and
- a detector for detecting whether the cover is covering the opening.

12. The device of claim 11 wherein:
the cover comprises a recess;
the detector is an infrared detector and is disposed on a first side of the recess;
an infrared source is disposed on a second side of the recess opposite the first side; and
the vessel comprises a wall that interposes the two sides of the recess when the cover is covering the vessel.

13. The device of claim 11 wherein:
the cover comprises a recess;
the detector is a visible light detector and is disposed on a first side of the recess;
a visible light source is disposed on a second side of the recess opposite the first side; and
the vessel comprises a wall that interposes the two sides of the recess when the cover is covering the vessel.

14. The device of claim 11 wherein an inner surface of the vessel comprises a food safe material.

15. The device of claim 11 wherein the cover further comprises a thermistor.

16. The device of claim 11 wherein the cover further comprises a controller for supplying current to the semiconductor device.

17. The device of claim 16 wherein the cover further comprises a computer readable memory encoded with instructions for:
the controller receiving a user-generated input from a switch; and
the controller supplying current to the semiconductor device if the detector detects the cover is covering the opening.

18. The device of claim 17 wherein:
the cover further comprises an indicator; and
the computer readable memory further comprises instructions for:
activating a first indicator state if the detector detects the cover is not covering the opening; and
activating a second indicator state if the controller is supplying current to the semiconductor device.

* * * * *